United States Patent
Smith et al.

(10) Patent No.: US 7,207,230 B2
(45) Date of Patent: Apr. 24, 2007

(54) HIGH-STABILITY INSTRUMENT MOUNTING SYSTEM FOR REPEATABLE FIELD TESTING OF EQUIPMENT

(75) Inventors: Christopher P. Smith, Woodstock, GA (US); David E. Morlan, Acworth, GA (US); Paul G. Anderson, Acworth, GA (US)

(73) Assignee: Crane Nuclear, Inc., Kennesaw, GA (US)

( * ) Notice: Subject to any disclaimer, the term of this patent is extended or adjusted under 35 U.S.C. 154(b) by 149 days.

(21) Appl. No.: 10/848,697

(22) Filed: May 19, 2004

(65) Prior Publication Data

US 2004/0261537 A1    Dec. 30, 2004

Related U.S. Application Data

(60) Provisional application No. 60/472,631, filed on May 22, 2003.

(51) Int. Cl.
 G01M 19/00  (2006.01)
 G01B 5/30   (2006.01)
 G01N 3/02   (2006.01)
(52) U.S. Cl. .................................... 73/866.5; 73/865.9
(58) Field of Classification Search ........ 73/1.08–1.13, 73/1.15, 1.79–1.81, 865.9, 866.5, 788; 33/783, 33/572
See application file for complete search history.

(56) References Cited

U.S. PATENT DOCUMENTS

| | | | |
|---|---|---|---|
| 2,663,085 A | 12/1953 | Ruge | |
| 4,507,871 A | 4/1985 | Meyer et al. | |
| 4,509,265 A * | 4/1985 | Donaldson | 33/549 |
| 4,856,327 A | 8/1989 | Branam et al. | |
| 4,911,004 A | 3/1990 | Leon | |
| 4,930,228 A | 6/1990 | Anderson et al. | |
| 4,936,150 A | 6/1990 | Burke et al. | |
| 5,099,700 A | 3/1992 | Morin et al. | |
| 5,123,283 A | 6/1992 | Duff et al. | |
| 5,142,906 A | 9/1992 | Smith | |
| 5,153,675 A * | 10/1992 | Beauchaine | 356/451 |
| 5,199,301 A | 4/1993 | Bauer | |
| 5,546,817 A | 8/1996 | Heiman | |
| 5,955,679 A | 9/1999 | Leon | |

FOREIGN PATENT DOCUMENTS

EP          390970 A  * 10/1990

* cited by examiner

*Primary Examiner*—Thomas P. Noland
(74) *Attorney, Agent, or Firm*—Womble Carlyle Sandridge & Rice, PLLC (57) ABSTRACT

An instrument mounting system for repeatable field testing of equipment or other test object, comprising a frame and an inner surface defined at least in part by the frame. Exactly three object contact points are disposed upon the inner surface, the three object contact points defining a plane.

12 Claims, 8 Drawing Sheets

HIGH-STABILITY INSTRUMENT MOUNTING SYSTEM FOR REPEATABLE FIELD TESTING OF EQUIPMENT

RELATED APPLICATIONS

This application is a non-provisional application of and claims benefit of Provisional Application No. 60/472,631, filed May 22, 2003, the content of which is incorporated herein in its entirety.

FIELD OF THE INVENTION

The present invention relates to strain, force, deflection, torque, and temperature measuring techniques, and more particularly, to improved structures for intermittently installed test instruments.

BACKGROUND OF THE INVENTION

Temporary instrumentation, other than dedicated designs that install into the structure of a specific machine, or on a specially designed bracket or boss incorporated into the machine, is usually mounted by clamping, strapping, or adhesive. Designs that are intended to be intermittently used and thus installed and removed as needed are typically mechanically clamped or fixtured to the tested object/machine. FIGS. 1 through 5 depict several devices of this type.

Figure 1:
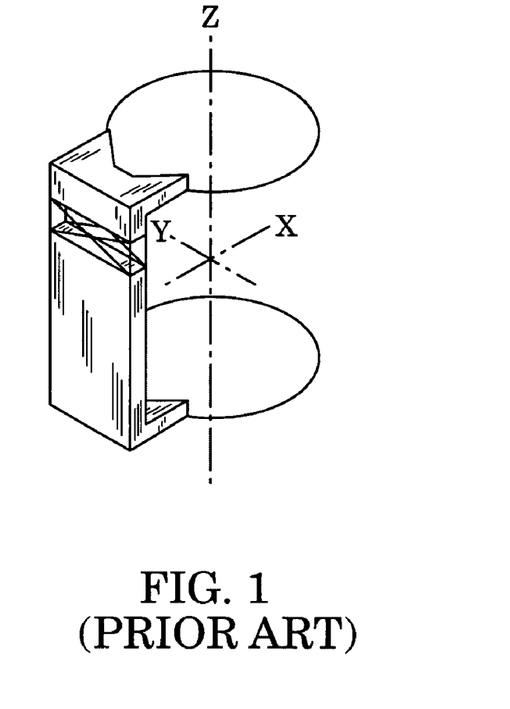
FIG. 1 depicts a generalized axial extensometer of the type used for material testing, and particularly for tensile testing of metals, the instrument being shown with blade edges for lines contact with the test object and elastic bands to secure the device to the test object at each end.
Figure 2:
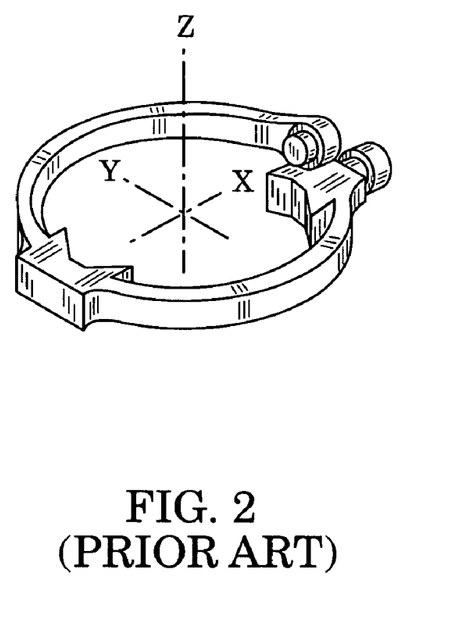
FIG. 2 depicts a diametric, or radial, extensometer as used on cylindrical test objects for measuring diametric dimension change, the device being clamped to the test object, but with a follower and its arm free except for their integral connection with the anvil piece.
Figure 3:
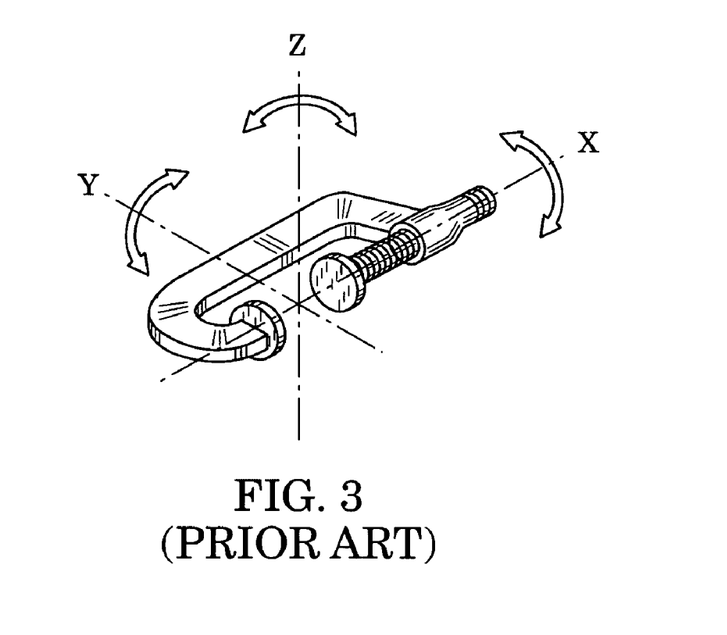
FIG. 3 depicts a second type of prior art diametric device, having the spindle turned to create a substantial clamping force on the part, which in turn produces tension and bending in the frame.
Figure 4:
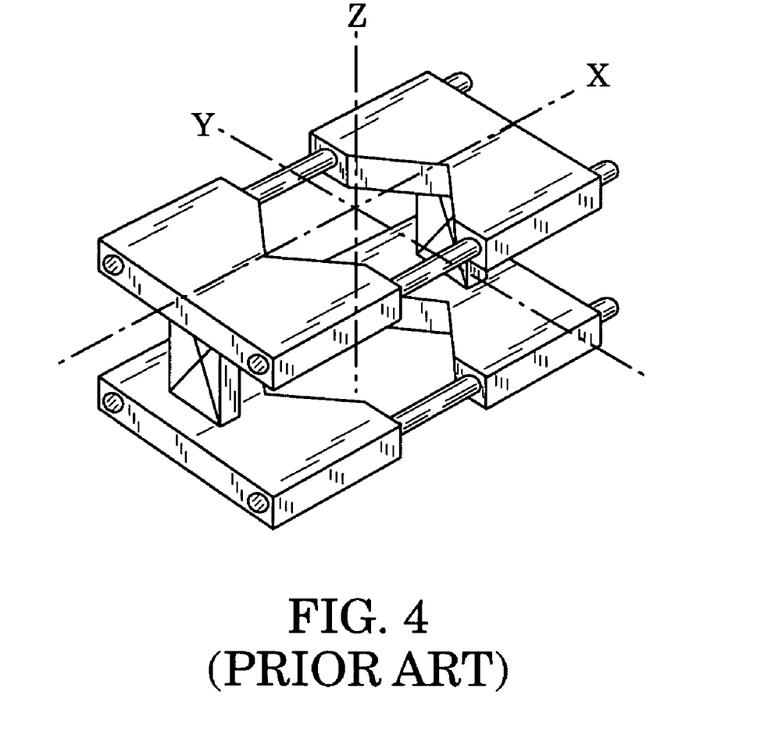
FIG. 4 depicts a prior-art device used on cylindrical shafts, formed as two parallel decks on the shaft perpendicular to its axis, for measuring the change in distance between the decks to infer axial strain.
Figure 5:
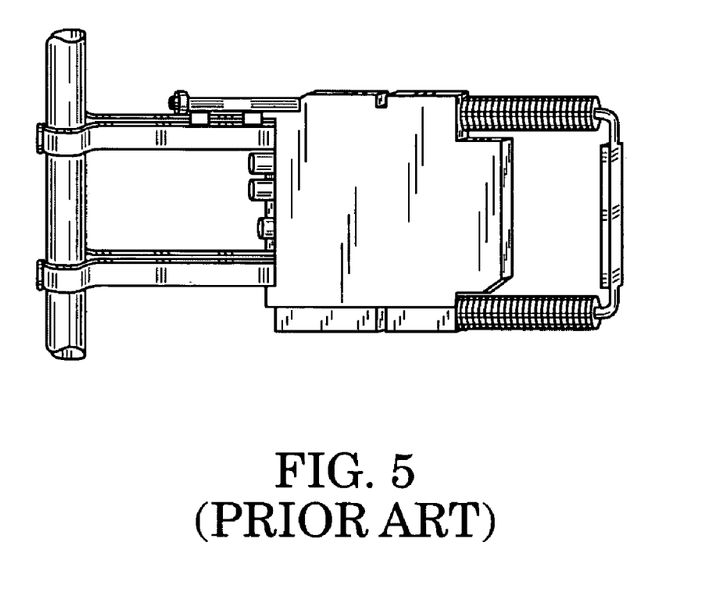
FIG. 5 illustrates a typical prior art materials-testing extensometer.

Briefly, FIG. 1 depicts one type of axial extensometer that is used for tensile testing of materials. Blade-type edges are in contact with the test object and elastic bands are used to secure the device to the test object. FIG. 2 depicts a diametric, or radial extensometer that is clamped to the test object. FIG. 3 is another type of diametric test device having a spindle that is used to create a clamping force on the test object. FIG. 4 depicts another prior art device comprising two parallel decks used to measure axial strain on cylindrical shafts. Finally, FIG. 5 is illustrative of a commercially-available extensometer having arms that clamp to a cylindrical shaft; however, this instrument has an offset center of gravity which can be problematic during field testing of equipment.

Figure 6:
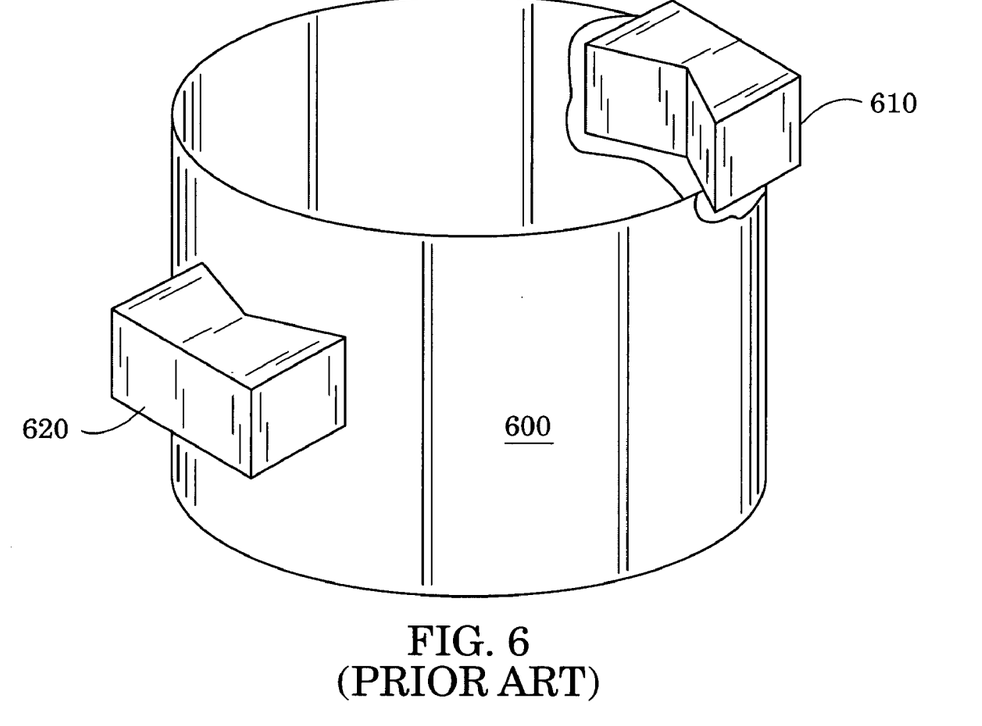
FIG. 6 illustrates the distributed contact effects common to "vee-block" type mounting frames, as seen on the prior art devices of FIGS. 2, 3, and 4.

While each of these devices has been developed for tensile and/or torsional testing, they are either delicate and error-prone, difficult to mount and use, are relatively imprecise, or a combination thereof. This is driven by the nature of these instruments as being temporarily installed, and generally designed for use with a range of test object sizes. For instance, as best seen in FIG. 6, the devices shown in FIGS. 2 through 4 have "vee-block" type distributed contact effects where the instrument has four lines of contact on the test object, each with significant area. This renders the exact gage length, or distance between reference points, indeterminate. It should be noted that strain and deflection-measuring devices typically depend on a precisely defined gage length or reference distance: The precision, stability, and repeatability of the gage length directly limits the performance of the device.

There have been many specialized extensometer designs produced to suit particular applications, often gaining some performance advantages over the generic types, but at the cost of narrow applicability. Yet, there are a number of problems that still exist. First, under vibration or acceleration test conditions, a device may slip or shift. This can cause shifts or other extraneous signals in the output of the device, and produce non-repeatability from test to test. Second, the ability of the instrument to re-acquire a specific mounting relationship on a part for reproducibility from test to test is needed to support calculated and calibrated transfer function equations, and for trending of measured values. That is, when the test object surface is complex or irregular (threads, splines, curved cylinders such as heat exchanger tubes, parts with complex strain fields due to keyways, adjacent fasteners, etc.), consecutive installations often result in the instrument contact areas, and thus the effective gage length, varying from test to test. Third, physical non-linearity and hysteresis (squirm) of the instrument can result. This is out-of-plane motion or distortion of the instrument frame or imperfect tracking of the motion of the test object surface.

SUMMARY OF THE INVENTION

The present invention is directed to a system and method for precise, repeatable, intermittent installation of test instrumentation on equipment.

The specification and drawings of U.S. Provisional Application No. 60/472,631, filed May 22, 2003, are hereby incorporated by reference in their entirety.

Generally, the instrument mounting system of the present invention comprises a frame assembly that defines a shape adaptable to the equipment or test object on which the system is to be mounted. Exactly three contact points are disposed on the inner surface of the frame assembly, the contact points defining a plane. At least one device is provided for measuring the relative motion between two or more points on the frame assembly or test object. One embodiment of the present invention provides a high-stability instrument mounting system for repeatable field testing of equipment. The system includes a frame having an arcuate portion and two arms defining an inner surface, the arms having free ends. Such a device would be most suitable for mounting about a cylindrical test body. Three object contact points are disposed on the inner surface, the three object contact points defining a plane having a centroid. The three object contact points are for contact with the equipment to be tested. One or more counterweights may be mounted to the frame so that the center of mass of the frame is created to coincide substantially with the centroid of the plane. In one embodiment, at least one recess is formed in the frame, and a strain element, or gage, is mounted in the recess for measuring the relative motion of points on a frame or test object, although as those skilled in the art will appreciate, there are other suitable mounting configurations. Additionally, there are other mechanical, optical, etc. devices which may be mounted on a frame or test object. When mounted in this fashion on the equipment to be tested, the frame or test object becomes translationally and rotationally stable with respect to the equipment.

In another embodiment, the high-stability instrument mounting system comprises a frame having an extended base portion and two arms defining an inner surface, the arms having free ends. Three object contact points are disposed on the inner surface of the frame, the three object contact points defining a plane having a centroid. Again, one or more counterweights may be mounted to the frame, wherein the center of mass of the frame is created to coincide substantially with the centroid of the plane. As in the first embodiment, at least one recess is formed in the frame, and a strain element is mounted in the recess for measuring deflection on the frame.

In another embodiment, the high-stability instrument mounting system comprises a ring-shaped frame defining an inner surface. Three object contact points are disposed on the inner surface of the frame, the three object contact points also defining a plane having a centroid.

In yet another embodiment, the high-stability instrument mounting system comprises a frame assembly having a pair of ring-shaped frames, each of the frames defining an inner surface. Again, three object contact points are disposed on the inner surface of each frame, the three object contact points defining a plane having a centroid within each frame. Two or more webs interconnect the pair of ring-shaped frames, so that interconnected, the planes of the frames are substantially parallel with one another and the inner surfaces of the frames are in substantial registration with one another. Also again, a strain element is mounted on at least one of the webs for measuring deflection on the frame.

These and other aspects of the present invention will become apparent to those skilled in the art after a reading of the following description of the preferred embodiments when considered in conjunction with the drawings. It should be understood that both the foregoing general description and the following detailed description are exemplary and explanatory only and are not restrictive of the invention as claimed.

DESCRIPTION OF THE PREFERRED EMBODIMENTS

Figure 7:
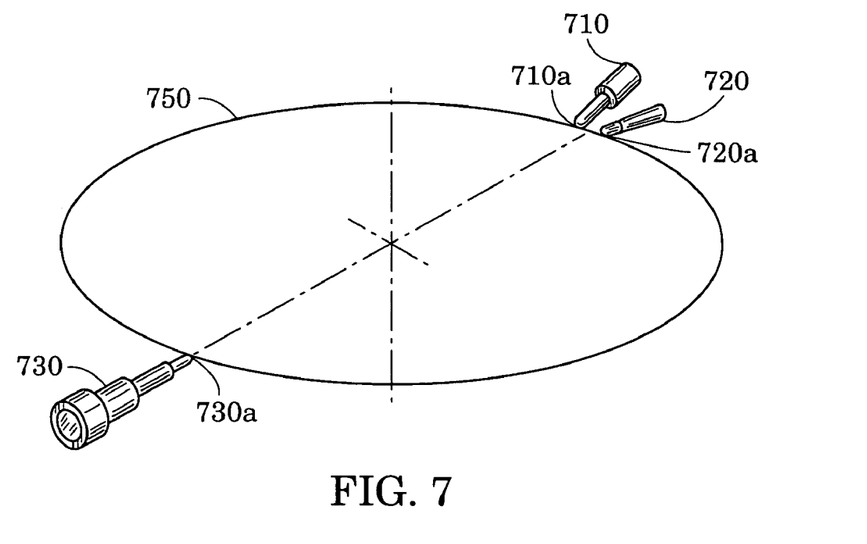
FIG. 7 illustrates the general concept of a three-pin instrument mounting frame according to the present invention, showing a first pin axially adjustable by a screw-drive, and diametrically opposed from a set of two additional pins, one fixed in the frame and the other spring-loaded.

Referring now to the drawings, and FIG. 7 in particular, the basic, and common principle of the present invention is shown. Unlike the prior art devices and mounting systems, the three-point mounting system of the present invention provides a high-stability instrument mounting system for repeatable field testing of equipment. First, the mounting system described herein forms a Euclidean plane that is defined by three contact points that lie on the plane. It has been found that a system, or device, that is supported on a three-point system is the simplest fixed structure, whereas a system that is supported on only one or two points is not fixed rotationally. Conversely, a system supported on more than three points is statically indeterminate with load distribution on the points being unknown. Where the three points are located on the surface of a three-dimensional test object and bear on generally opposing faces of the object, the system becomes translationally and rotationally fixed in all axes with respect to the tested object. As shown schematically in FIG. 7, a first pin 710 (a spring-loaded pin) and a second pin 720 (a fixed pin), both close together on one surface of a test object, oppose a third pin 730 (a spindle runner, or screw drive) on the opposite surface of a hypothetical test object. This creates a plane 750 on which three contact points 710a, 710b, and 710c all lie.

Figure 8:
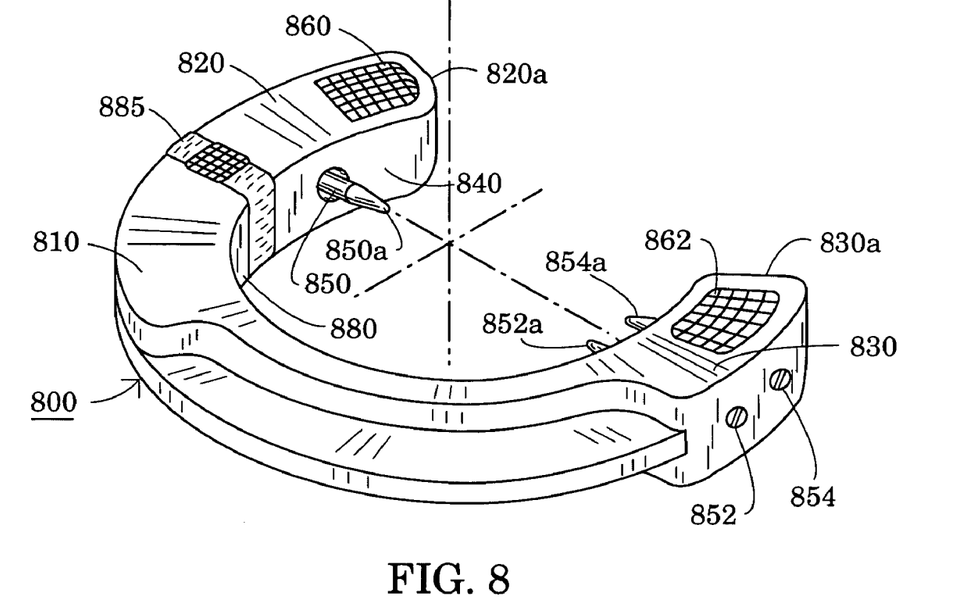
FIG. 8 depicts one embodiment of the present invention, shown as a diametric extensometer.

Turning now to FIG. 8, a first embodiment of the high-stability instrument mounting system of the present invention is shown. Shown generally as 800, the mounting system comprises a frame 810 having an arcuate portion and two arms 820, 830 defining an inner surface 840. Arms 820 and 830 have free ends 820a, 830a. This system surrounds the test object with the arcuate, or semicircular, frame 810 that holds three pins 850, 852, and 854 that define three object contact points on the inner surface 840 of the frame 810. Pin 850, mounted in arm 820, is desirably a spindle runner that can be adjusted translationally inward to bring the three pins 850, 852, 854 (and, thus, the three object contact points) into contact with the test object and to apply a force acting radially inward on the test object. As will be appreciated, the three object contact points define a plane having a centroid corresponding the center of the test object. One or more counterweights 860, 862 may be mounted in or on the frame 810 to create a center of mass near the centroid of the plane defined by the three points. As referred to hereinabove, one of either pin 852 or pin 854 is solidly mounted in the frame to directly transmit a radial mounting force. The other of the two pins is spring-loaded to provide a lower radial force, and is intended only to maintain the location of the frame 810 in the plane. In the embodiment shown in FIG. 8, at least one small shear web structure, or recess 880 is formed in the frame 810. A strain element 885 is mounted in the recess 880 to measure the relative motion of points on the frame 810; although as those skilled in the art will appreciate, there are other suitable monitoring configurations. Additionally, there are other mechanical, optical, etc. devices which may be mounted on the frame 810. By monitoring changes in the diametric expansion or contraction of the test object, it is then possible to calculate, via the appropriate transformation equations, the radial force.

Figure 9:
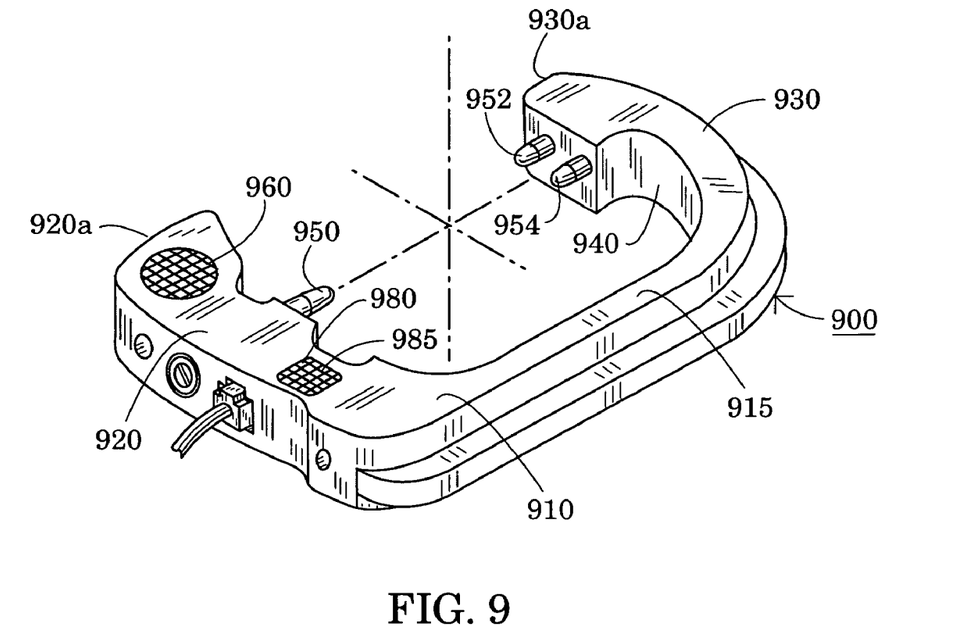
FIG. 9 depicts an alternate embodiment of the device of FIG. 8 adapted to fit a range of test object sizes.

Referring to FIG. 9, an alternative embodiment 900 of the high-stability instrument mounting system of FIG. 8 is shown. This mounting system is similar in construction to the mounting system 800 of FIG. 8, comprising a frame 910 having an extended base portion 915 and two arms 920, 930 defining an inner surface 940, the arms 920, 930 having free ends 920a, 930a. Three object contact points are created by three pins 950, 952, 954 on the inner surface 940, the three object contact points defining a plane having a centroid. One or more counterweights 960 may be mounted to the frame 910, wherein a center of mass of the frame or test object is created to coincide substantially with the centroid of the plane. At least one recess 980 is formed in the frame 910, and a strain element 985 is mounted in the recess 980. This embodiment is functionally similar to the previous embodiment, except that the frame 910 is extended in length and narrowed so that the arms 920 and 930 can accommodate wider ranges of test object sizes and shapes.

Figures 10, 11:
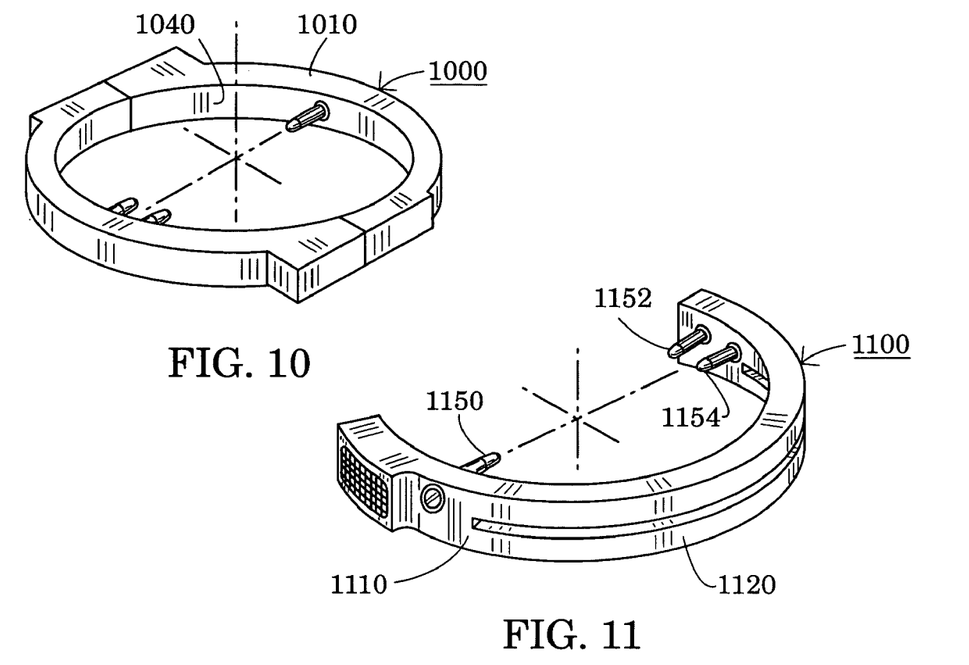
FIG. 10 depicts a second embodiment of the present invention, shown as a single-deck, three-pin frame.
FIG. 11 depicts an alternative embodiment of the device of FIG. 10.

Another embodiment of the mounting system of the present invention is shown in FIG. 10 as 1000. This embodiment 1000 comprises a ring-shaped frame 1010 defining an inner surface 1040. Three object contact points are created on the inner surface 1040 of the frame 1010, defining a plane having a centroid. This mounting system is of the type that could be used to mount another instrument (not shown) or to hold a lightweight, fragile device (not shown) such as a small extensometer element or an optical component to a cylindrical test object for diametric measurement of the test object.

Another embodiment of the mounting system of the present invention is shown in FIG. 11. Shown generally as 1100, this system is constructed with a three-pin frame 1110 with an integral reference arm 1120 that references one pin 1150 to the diametrically-opposed surface of the test object through pins 1152 and 1154. This mounting construction would be used as a diametric extensometer by mounting a deflectometer or proximity element (not shown) on the reference arm 1120.

Figure 12:
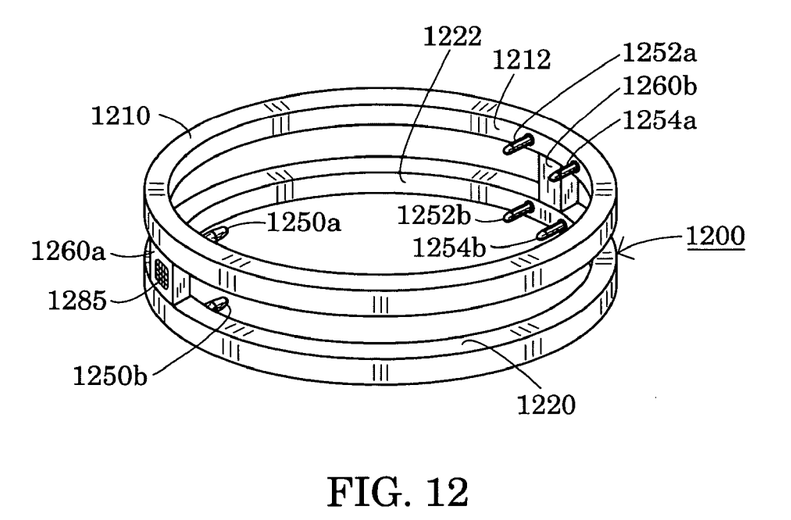
FIG. 12 depicts a third embodiment of the present invention, shown as a pair of three-pin frames.

Yet another embodiment of the present invention is shown in FIG. 12. Shown generally as 1200, this high-stability instrument mounting system is intended for repeatable field testing of equipment. This system comprises a frame assembly having multiple, shown here as a pair of, ring-shaped frames 1210, 1220, each of the frames 1210, 1220 defining an inner surface 1212, 1222. Pins 1250a, 1250b, 1252a, 1252b, 1254a, and 1254b form three object contact points on the inner surface 1212, 1222 of each frame. The three object contact points further define a plane having a centroid within each frame 1210, 1220. Two webs 1260a, 1260b interconnect the adjacent ring-shaped frames to define two parallel transverse planes through the test object as well as a fixed rotational relationship of each plane to the test object. At least one element or probe 1285 is mounted on at least one of the webs 1260a, 1260b. This mounting system would typically be used as an axial and/or torsional extensometer, employing one set of strain elements to transduce changes in the relative angular or axial position of the two plane sections.

Figure 13:
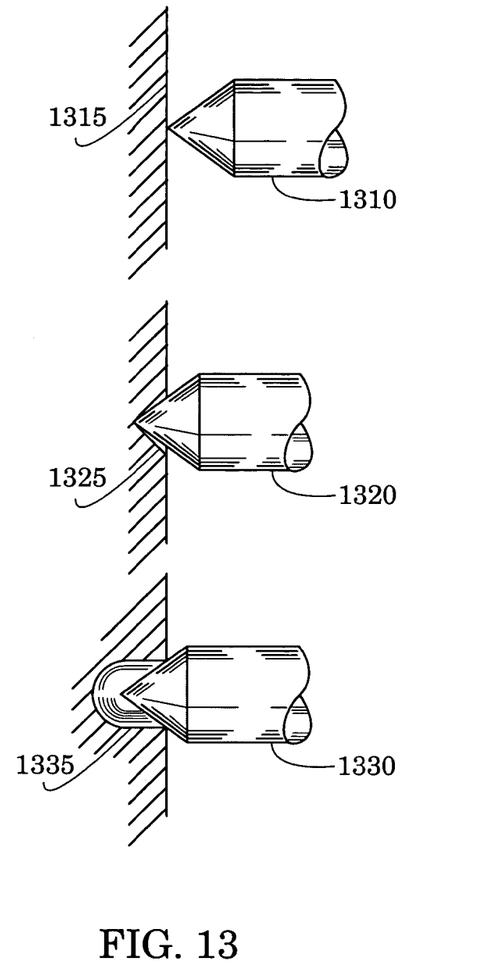
FIGS. 13 and 14 are exemplary of possible pin tip and part surface configurations for the embodiments of the present invention.
Figure 14:
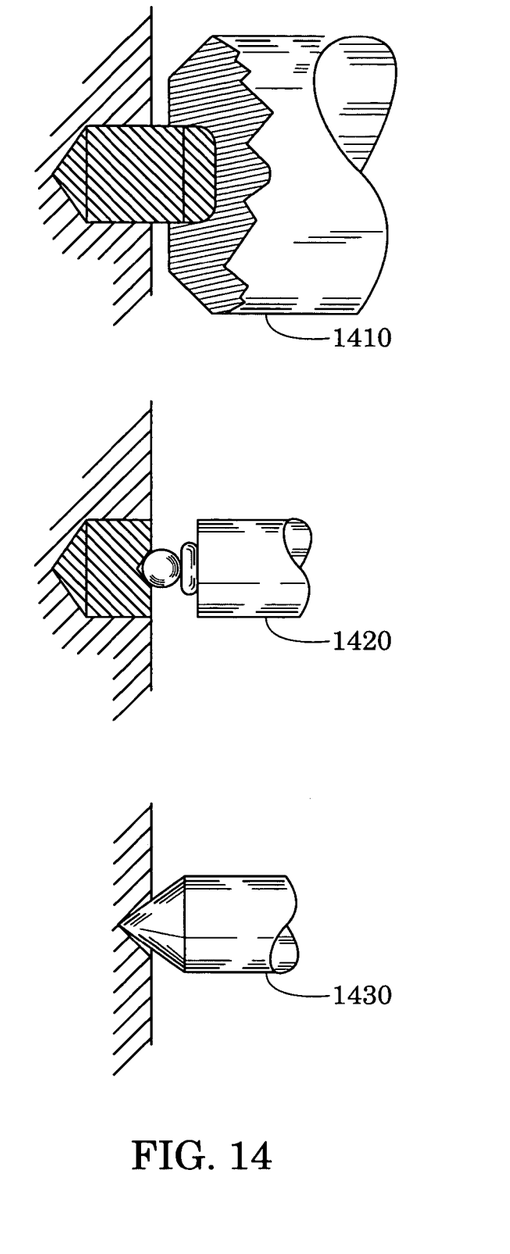

Another aspect of the present invention relates to the mounting pin geometries and test object configurations that may be employed with the various embodiments of the present invention. Six exemplary pin and test object surface configurations are shown in FIGS. 13 and 14. As shown in FIG. 13, one suitable mounting configuration employs a conical pin 1310 having a relatively sharp point that would contact with a substantially flat test object surface 1315. Alternatively, a pin 1320 with a conical tip could be mounted to a test object surface having a conical recess 1325 dimensioned to receive the conical tip of the pin 1320. In another alternative configuration, a pin 1330 having a more rounded tip could be mounted to a test object surface have a rounded recess 1335 adaptable to receiving the rounded tip. Turning to FIG. 14, alternative mounting configurations are shown as 1410, 1420, and 1430, each mounting configuration illustrating a pin geometry and surface geometry configuration.

Figure 15:
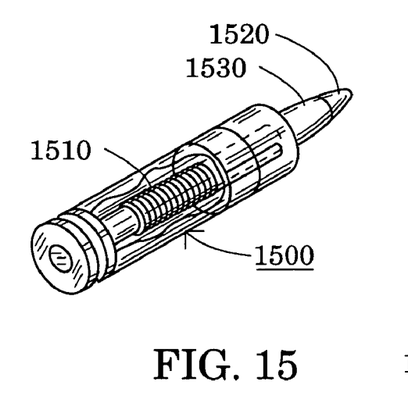
FIG. 15 illustrates an exemplary embodiment of a spindle runner.
Figure 16:
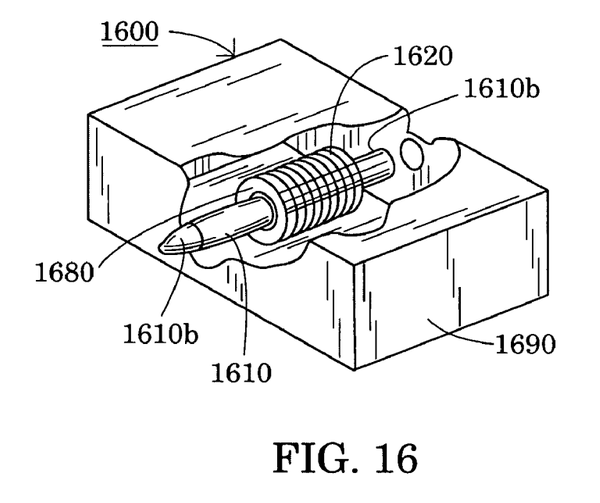
FIG. 16 illustrates an exemplary embodiment of a soft pin.

In addition to the pin and surface mounting configurations, several suitable spindle runner and "soft" pin configurations have been found suitable. Referring to FIG. 15, a conventional spindle runner 1500 construction is shown. The spindle runner 1500 comprises a pin having a threaded portion 1510, a point, or contact portion 1520, and an extension 1530. As shown in FIG. 16, one suitable soft pin construction is shown. A spring-loaded pin 1610 is mounted in a cylindrical recess 1680 that is formed in the inner surface wall of the frame 1690 of the mounting system. When relaxed, spring 1620 pushes the pin 1610 outwardly so that the tip 1610a is in soft contact with the test object (not shown). When the spring 1620 is compressed, the pin 1610 is pushed into the recess 1680. As those skilled in the art will appreciate, the amount of required force, or load, to be exerted by the spring is dependent upon the mass of the instrument.

Figure 17:
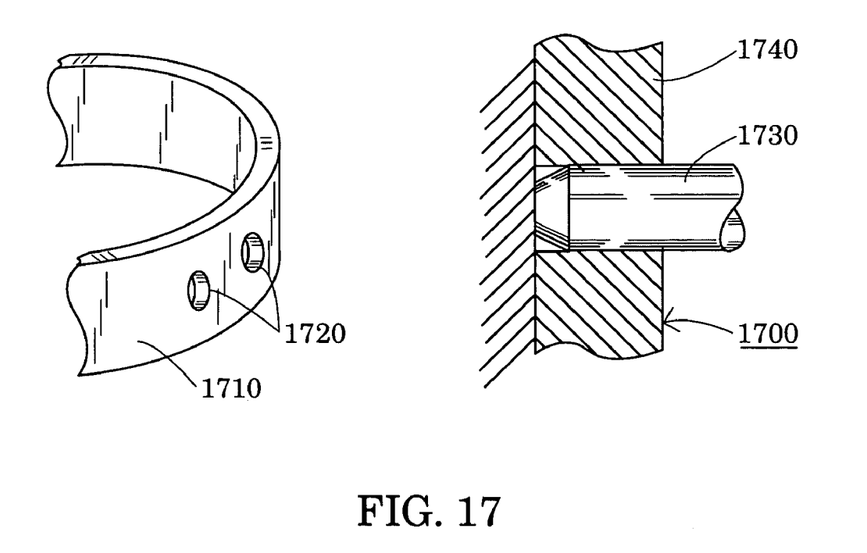
FIG. 17 illustrates a non-invasive configuration for pin mounting points on a test object.

Referring to FIG. 17, there is shown a "non-invasive" mounting configuration 1700. A band 1710 of metal or plastic, either tightened around or molded around the test object, replaces the need for recesses or indentions in the surface of the test body (shown above in FIGS. 13 and 14). Radial bores 1720 (positioned for three-point contact) are formed through the wall of the band 1710. Positioned rigidly in place, pins 1730 from the mounting systems described herein could be inserted through the bores 1720 to precisely position the mounting system.

Figure 18:
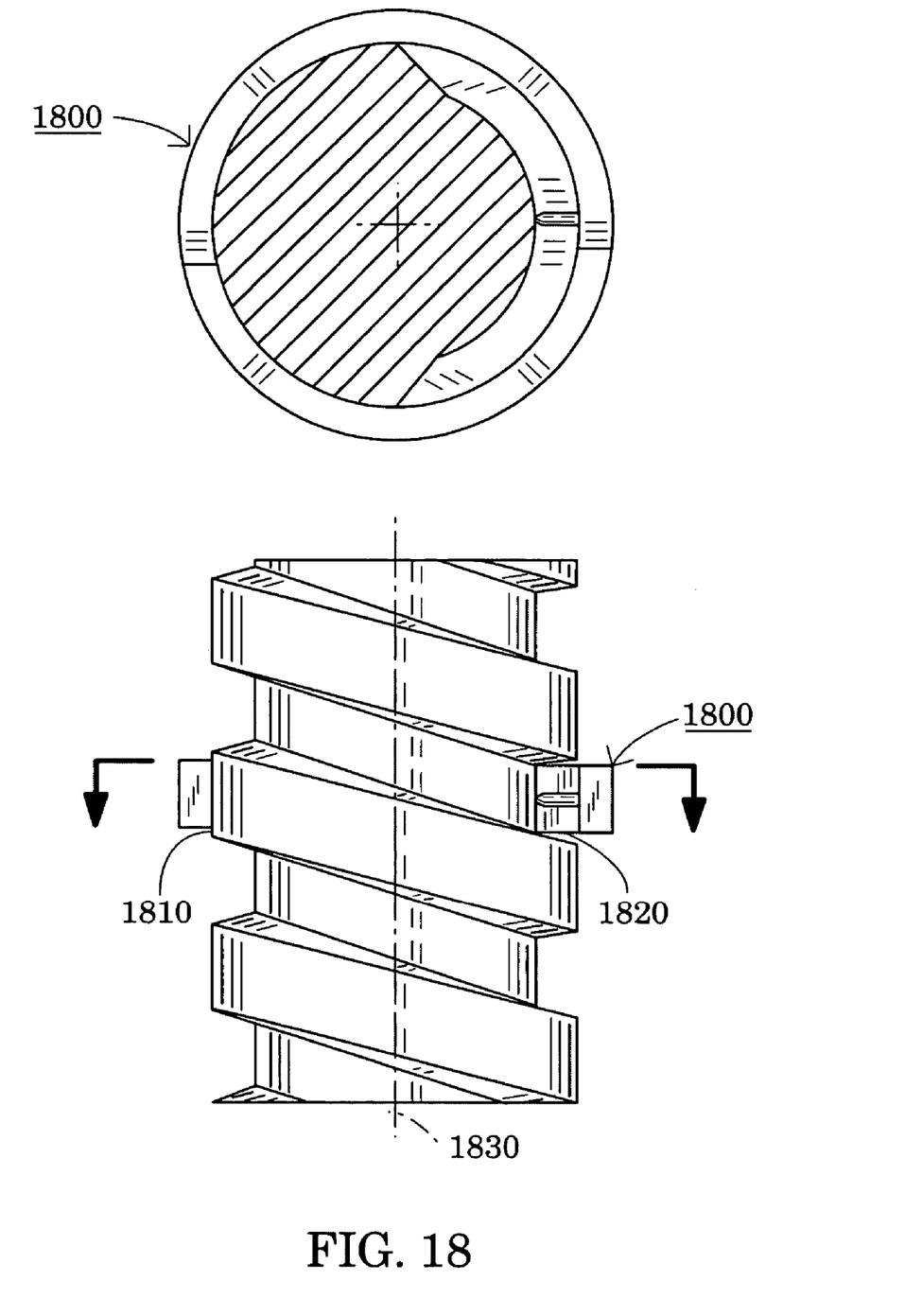
FIG. 18 illustrates a pin mounting scheme for a cylindrical, threaded test object.

Finally, as shown in FIG. 18, a mounting configuration 1800 for a cylindrical, threaded test object is shown. This configuration 1800 is suitable for a threaded test object in which the thread has an odd number of leads, causing a thread crown 1810 to be diametrically opposed by a thread root 1820 on any plane transverse to a cylinder's central axis 1830. Where the diametrical plane passes through a crown and a root, the mounting configuration would encompass one mounting point on a crown and one mounting point on a root. In such a configuration, the form and area of the plane is calculated geometrically and adjusted, as necessary, by empirical testing to produce needed transformation equations for interpretation of deformation measurements with respect to their causal forces.

The invention is not limited to or by the depicted pin and surface geometries and configurations.

Certain modifications and improvements will occur to those skilled in the art upon a reading of the foregoing description. It should be understood that all such modifications and improvements have been deleted herein for the sake of conciseness and readability but are properly within the scope of the following claims.

We claim:

1. An instrument mounting system for repeatable field testing of equipment or other test object, comprising:
    (a) a frame and an inner surface defined at least in part by said frame;

(b) exactly three object contact points projecting inwardly relative to the inner surface of the frame and defining a plane, each of the object contact points comprising a pin; and (c) a measuring device mounted on the frame.

2. The mounting system of claim 1, wherein said frame comprises a frame assembly selected from the group consisting of: a frame comprising an arcuate portion and two arms; a frame comprising a base portion and two arms; a ring-shaped frame; a frame assembly comprising a plurality of ring-shaped frames; and a frame assembly defining a generally concave surface.

3. The mounting system of claim 1, wherein said frame comprises a frame assembly comprising a plurality of ring-shaped frames, each of said frames defining an inner surface with three object contact points, and said system further comprises two or more webs interconnecting adjacent ring-shaped frames, wherein when interconnected the planes defined by said three object contact points of each of said frames are substantially parallel with one another and said inner surfaces of said ring-shaped frames are in substantial registration.

4. The mounting system of claim 1, wherein at least one of said pins is a fixed pin.

5. The mounting system of claim 1, wherein at least one of said pins is a spring-loaded pin.

6. The mounting system of claim 1, wherein at least one of said pins is an adjustable spindle.

7. The mounting system of claim 1, wherein said pins comprise a fixed pin, a spring-loaded pin, and an adjustable spindle.

8. The mounting system of claim 7, wherein said adjustable spindle is substantially diametrically opposed to said fixed pin and said spring-loaded pin.

9. The mounting system of claim 1, further comprising at least one counterweight mounted to the frame.

10. The mounting system of claim 1, further comprising at least one counterweight mounted to said frame.

11. The mounting system of claim 1, wherein the measuring device is selected from the group consisting of a strain element, a probe, and an optical component.

12. The mounting system of claim 11, wherein the measuring device is mounted to said frame.

* * * * *